United States Patent
Bharat et al.

(10) Patent No.: US 10,317,510 B2
(45) Date of Patent: Jun. 11, 2019

(54) APPARATUS FOR OBTAINING TRIGGER SIGNALS FROM ULTRASOUND SYSTEMS

(71) Applicant: KONINKLIJKE PHILIPS N.V., Eindhoven (NL)

(72) Inventors: Shyam Bharat, Arlington, MA (US); Ameet Kumar Jain, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 155 days.

(21) Appl. No.: 15/302,077

(22) PCT Filed: Apr. 3, 2015

(86) PCT No.: PCT/IB2015/052454
§ 371 (c)(1),
(2) Date: Oct. 5, 2016

(87) PCT Pub. No.: WO2015/155655
PCT Pub. Date: Oct. 15, 2015

(65) Prior Publication Data
US 2017/0184701 A1    Jun. 29, 2017

Related U.S. Application Data

(60) Provisional application No. 61/978,201, filed on Apr. 11, 2014.

(51) Int. Cl.
| | |
|---|---|
| *A61B 8/00* | (2006.01) |
| *G01S 7/00* | (2006.01) |
| *A61B 8/08* | (2006.01) |
| *G01S 7/52* | (2006.01) |
| *G01S 15/89* | (2006.01) |

(52) U.S. Cl.
CPC ............ *G01S 7/003* (2013.01); *A61B 8/0841* (2013.01); *A61B 8/4472* (2013.01); *A61B 8/461* (2013.01); *A61B 8/54* (2013.01); *G01S 7/52017* (2013.01); *G01S 15/8915* (2013.01)

(58) Field of Classification Search
None
See application file for complete search history.

(56) References Cited

U.S. PATENT DOCUMENTS

| | | | | |
|---|---|---|---|---|
| 7,730,242 B2 * | 6/2010 | Tsuchiya | ............... | G06F 13/385 370/241 |
| 2006/0092930 A1 * | 5/2006 | Shah | ..................... | H04L 67/125 370/389 |
| 2013/0041252 A1 | 2/2013 | Vignon et al. | | |

(Continued)

OTHER PUBLICATIONS

Wang et al: "A High-Speed Photoacoustic Tomography System Based on a Commercial Ultrasound and a Custom Transducer Array"; Photons Plus Ultrasound:Imaging and Sensing 2010, Proc. of SPIE, vol. 7564, 2010, pp. 756424-1-75624-9.

*Primary Examiner* — Hovhannes Baghdasaryan (57) ABSTRACT

An adaptor device includes a first connector (106) configured to interface with an ultrasound probe and a second connector (108) configured to interface with an ultrasound console. An array of lines (120) connects the first connector to the second connector. A pulse generator or generators (110, 112) are configured to output trigger signals responsive to a signal on one or more of the array of lines. An external output (114, 116) is configured to output the trigger signals.

17 Claims, 6 Drawing Sheets

(56) References Cited

U.S. PATENT DOCUMENTS

2014/0007690 A1* 1/2014 Hirota .................. A61B 8/14
                   73/632
2014/0024928 A1  1/2014 Boctor et al.

* cited by examiner

APPARATUS FOR OBTAINING TRIGGER SIGNALS FROM ULTRASOUND SYSTEMS

CROSS-REFERENCE TO PRIOR APPLICATIONS

This application is the U.S. National Phase application under 35 U.S.C. § 371 of International Application No. PCT/IB2015/052454, filed on Apr. 3, 2015, which claims the benefit of U.S. Provisional Patent Application No. 61/978,201, filed on Apr. 11, 2014. These applications are hereby incorporated by reference herein.

BACKGROUND

Technical Field

This disclosure relates to medical instruments and more particularly to an apparatus configured to connect to ultrasound systems to enable trigger signals or timing signals to be output for use by other devices or equipment.

Description of the Related Art

In ultrasound sensing technology, precise timing information in the form of frame and line trigger signals is required to determine the location of a tracked tool in ultrasound (US) image space. In many US scanners (e.g., portable US systems), the frame and line trigger signals are not available externally to the US system. To make measurements to estimate the axial and lateral (and elevational, if three-dimensions (3D) are available) positions of the tracked tool in the US image, precise timing information is required from the US imaging probe, in the form of frame and line trigger signals.

Ultrasound tracking technology estimates the position of a passive ultrasound sensor (e.g., PZT, PVDF, copolymer or other piezoelectric material) in a field of view (FOV) of a conventional diagnostic B-mode image by analyzing the signal received by the sensor as the beams of the imaging probe sweep the FOV. Time-of-flight measurements provide the axial/radial distance of the PZT sensor from the imaging array, while amplitude measurements and knowledge of the beam firing sequence provide the lateral/angular position of the sensor. When used with 3D transducers (i.e., 2D matrix arrays), the elevational position of the sensor can also be obtained in a similar manner. Therefore, the 3D position of the sensor can be estimated in real-time, provided it is present within the FOV of the imaging transducer. The sensor passively listens to the ultrasound waves impinging on it as the imaging probe's beams sweep the field of view. Analysis of these signals yields the position of the sensor on a tool in the frame of reference of the ultrasound image. The position can then be overlaid on the ultrasound image for enhanced tool visualization, and the positions and their histories can be logged for tracking, segmentation, and other applications.

SUMMARY

In accordance with the present principles, an adaptor device includes a first connector configured to interface with an ultrasound probe and a second connector configured to interface with an ultrasound console. An array of lines connects the first connector to the second connector. A pulse generator or generators are configured to output trigger signals responsive to a signal on one or more of the array of lines. An external output is configured to output the trigger signals.

Another adaptor device includes a first connector configured to interface with an ultrasound probe and a second connector configured to interface with an ultrasound console. An array of lines is formed on a substrate and connects the first connector to the second connector. A frame pulse generator is configured to output a frame trigger signal responsive to a signal on a line of the array of lines designated to indicate a new frame. A line pulse generator is configured to output a line trigger signal responsive to line signals on the array of lines. An external output is configured to output the frame and line trigger signals.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with exemplary embodiments of the present invention, an intermediate adaptor device or apparatus is provided that can interface between an ultrasound (US) probe and a US console or workstation. The adapter provides frame and line trigger signals as outputs, while maintaining connectivity of the US probe to the US console. The present principles can enable ultrasound sensing technology across a wide variety of US systems in the market by providing a simple and cost-effective adapter device that accesses and outputs these trigger signals. The adapter device provides easy implementation of the US sensing technology on all types of US systems, which do not provide pre-designed external access to the needed trigger signals.

In one embodiment, the adaptor device includes a plurality of ports. In one particularly useful embodiment four ports are provided. One port connects to the US probe (e.g., all channels). These channels are directly made available to the US console via a second port. Note that the signal flow from the US console to the US probe is also maintained. Thus, functionally, the way in which the US probe connects to the US system is unchanged. This makes the adapter device suitable for application on all devices. In addition, the frame and line trigger signals are estimated from individual channels and made available as outputs via externally accessible ports.

Multiple embodiments for the adaptor device are described, and depend on equipment features, for example, where the beamforming occurs (probe or console) or the type of interfaces. In another embodiment, the adaptor device works with wireless US systems.

It should be understood that the present invention will be described in terms of medical instruments; however, the teachings of the present invention are much broader and are applicable to any multiple channel system where trigger signals need to be employed for other equipment or signal processing. In some embodiments, the present principles are employed in tracking or analyzing complex biological or mechanical systems. In particular, the present principles are applicable to internal tracking procedures of biological systems and procedures in all areas of the body such as the lungs, gastro-intestinal tract, excretory organs, blood vessels, etc. The elements depicted in the FIGS. may be implemented in various combinations of hardware and/or software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Figure 1:
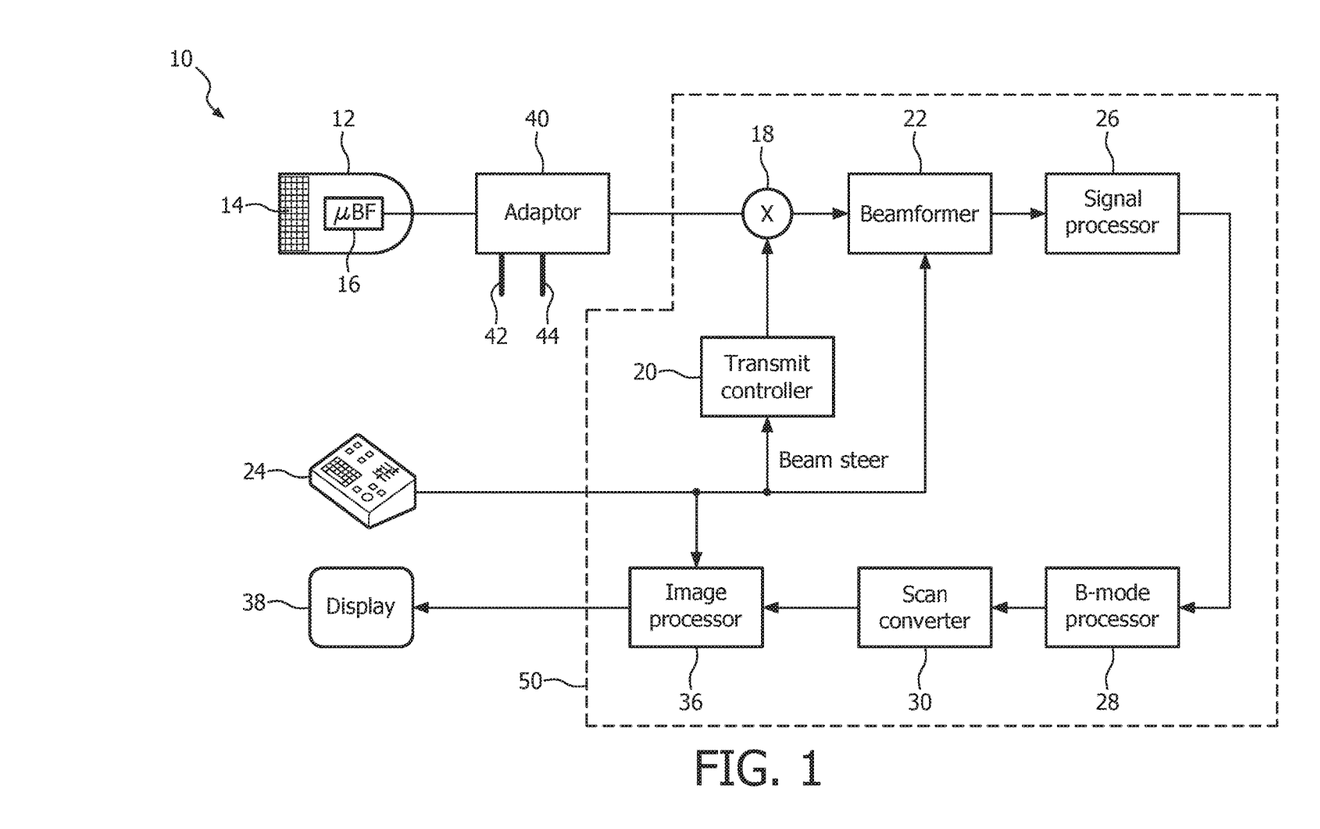
FIG. 1 is a block diagram showing an ultrasound system with preliminary beamforming in a probe and including an adaptor device in accordance with one embodiment.

Referring now to the drawings in which like numerals represent the same or similar elements and initially to FIG. 1, an ultrasound imaging system 10 constructed in accordance with the present principles is shown in block diagram form. The ultrasound system 10 includes a transducer device or probe 12 having a transducer array 14 for transmitting ultrasonic waves and receiving echo information. The transducer array may be configured as, e.g., linear arrays or phased arrays, and can include piezoelectric elements or capacitive micromachined ultrasonic transducers (CMUT) elements. The transducer array 14, for example, can include a two dimensional array (as shown) of transducer elements capable of scanning in both elevation and azimuth dimensions for 2D and/or 3D imaging.

In the embodiment shown, the transducer array 14 is coupled to a microbeamformer 16 in the probe 12, which controls transmission and reception of signals by the transducer elements in the array. The microbeamformer 16 may be integrated with the transducer device 12 and is coupled to a transmit/receive (T/R) switch 18, which switches between transmission and reception and protects a main beamformer 22 from high energy transmit signals. In some embodiments, the T/R switch 18 and other elements in the system can be included in the transducer probe rather than in a separate ultrasound system base. The transmission of ultrasonic beams from the transducer array 14 under control of the microbeamformer 16 is directed by a transmit controller 20 coupled to the T/R switch 18 and the beamformer 22, which may receive input from the user's operation of a user interface or control panel 24.

One function controlled by the transmit controller 20 is the direction in which beams are steered. Beams may be steered straight ahead from (orthogonal to) the transducer array 14, or at different angles for a wider field of view. The partially beamformed signals produced by the microbeamformer 16 are coupled to a main beamformer 22 where partially beamformed signals from individual patches of transducer elements are combined into a fully beamformed signal.

An adaptor device 40 is coupled between the probe 12 and a US console 50, although other configurations are possible for the placement of the adaptor, e.g., in the console 50, in the probe 12 or at another location (e.g., where wireless communication is employed). The adaptor device 40 is selectively removable and may include connectors for interfacing/communicating to/with both the US probe 12 and the US console 50. The adaptor device 40 outputs frame trigger signals on line or port 42 and line trigger signals on line or port 44, while maintaining the connectivity of the US probe 12 and to the console 50. The inputs to the adaptor device 40 include a connection to the US probe 12, which may include a standard multi-pin port. This multi-pin port also serves as an output port, for communication from the console 50 to the US probe 12. The adaptor device 40 may connect to the US console 50 by a universal serial bus (USB) or other connection type, depending on US system specifications. The USB (or other) port also serves as an input port, for communication from the US console 50 to the probe 12.

In some embodiments, the adaptor device 40 could be completely physically integrated within the probe 12, within the scanner or console 50, etc. In one embodiment, the adaptor device 40 may be designed to fit into an external fixture, e.g., a table or other mounted location. In such a case, the adaptor device 40 is integrated into the fixture, and may include a (wired or wireless) link to the console 50. This fixture could have additional links for signal communication to other tracking systems/software. The adaptor device 40 may include wired or wireless connections to the probe 12, to the console 50 and for transmitting frame trigger signals and/or line trigger signals to other devices.

The beamformed signals from beamformer 22 are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding and noise elimination. The processed signals are coupled to a B mode processor 28, which can employ amplitude detection for the imaging of structures in the body. The signals produced by the B mode processor 28 are coupled to a scan converter 30. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The scan converter 30 can convert echoes which are received from points in a common plane in a volumetric region of the body into an ultrasonic image of that plane. 2D or 3D images are coupled from the scan converter 30 to an image processor 36 for further enhancement, buffering and temporary storage for display on an image display 38. An image processor 36 can generate graphic overlays for display with the ultrasound images. These graphic overlays or parameter blocks can contain, e.g., standard identifying information such as patient name, date and time of the image, imaging parameters, frame indices and the like. For these purposes, the image processor 36 receives input from the user interface 24, such as a typed patient name. The user interface 24 can also be coupled to other components for selection and control of a display of multiple multiplanar reformatted (MPR) images, etc.

Display 38 is included for viewing internal images of a subject (patient) or volume. Display 38 may also permit a user to interact with the system 10 and its components and functions, or any other element within the system 10. This is further facilitated by the interface 24, which may include a keyboard, mouse, a joystick, a haptic device, or any other peripheral or control to permit user feedback from and interaction with the system 10.

The frame and line trigger signals from lines 42 and 44 can be output to a plurality of different devices for timing purposes or other applications. The frame and line trigger signals from lines 42 and 44 can be constructed in a plurality of ways depending on where the initial beamforming occurs.

Figure 2:
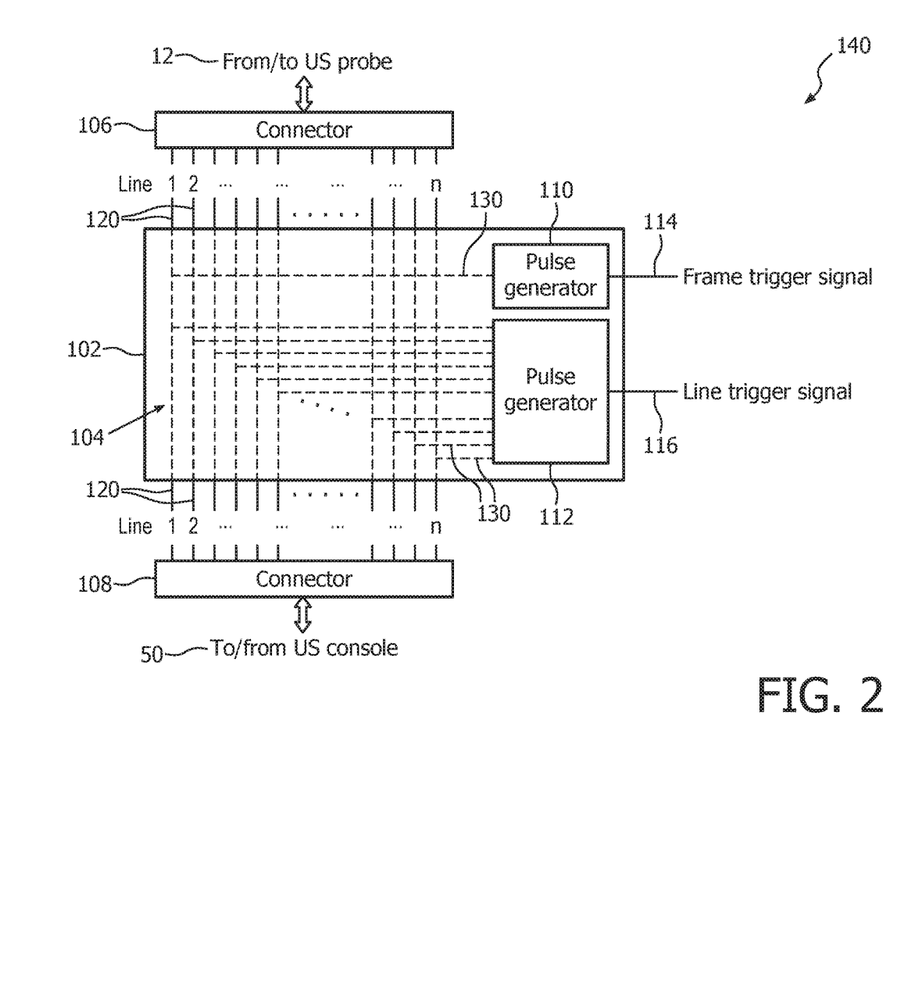
FIG. 2 is a schematic block diagram showing an adaptor device with connectors in accordance with one embodiment.

Referring to FIG. 2 with continued reference to FIG. 1, if the preliminary beamforming occurs in the US probe 12, a possible embodiment may include an adaptor device 140. Individual channels 120 or lines 1-$n$ from the probe 12 are input to the adaptor 140 through a connector 106. The signals from the individual channels 120 of an image are employed to construct a frame trigger signal 114 and line trigger signals 116. For example, the signal corresponding to a first line (line 1) can be used to generate the frame trigger signal 114. Similarly, the signal from every line (lines 1-$n$) is used to generate line trigger signals 116. The frame and line trigger signals 114, 116 are output from the adaptor device 140 through ports which are accessible externally. The individual US beams are also output and connect directly to the US console 50 through a connector 108. Thus, the US imaging functionality remains unaltered.

The adaptor device 140 may include a semiconductor chip or printed circuit board (PCB) 102 onto which a plurality of metallizations 104 are formed using processing techniques known in the art of semiconductor device or PCB fabrications. The adaptor device 140 may be formed on a substrate, such as a semiconductor, ceramic, prepreg board, etc. In the embodiment depicted in FIG. 2, pulse generator circuits 110 and 112 may be formed using semiconductor processing concurrently during the formation of the metallizations 104. Alternately, the pulse generators 110, 112 may be added by chip bonding or other process. Metallizations 104 may include other components for switching and multiplexing signals (e.g., transistors, logic gates, etc.).

Channels 120 are interconnected to lines 130, which connect to the pulse generators 110, 112. The interconnections between channels 120 and lines 130 may include direct connections, switches, multiplexers, etc. Upon receiving the signals on channels 120, lines 130 provide input to the respective pulse generator 110, 112. The pulse generators 110, 112 may act as a repeater and simply output the signal on the channel 120. Alternately, the pulse generators 110, 112 can condition the signal to provide an appropriate output depending on the use of the signal. For example, the input signal may be amplified, substituted for a different output current or voltage, change its phase, delay the signal, etc. to output the frame trigger signal 114 or the line trigger signals 116.

Figure 3:
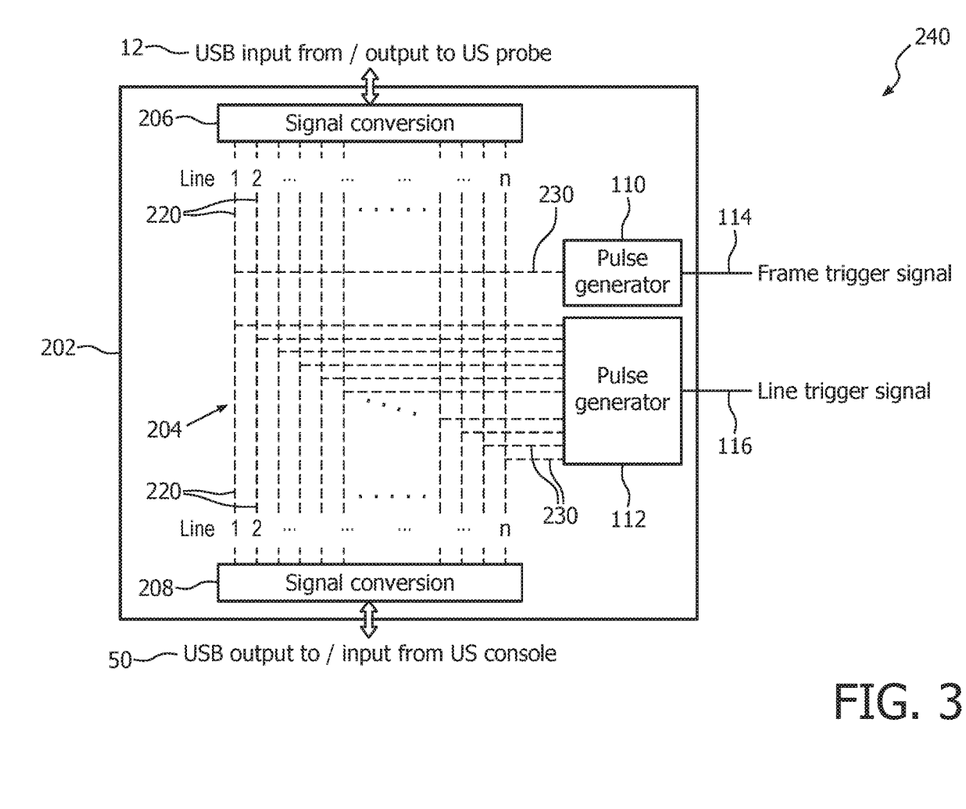
FIG. 3 is a schematic block diagram showing an adaptor device with standard port connections (e.g., USB) in accordance with another embodiment.

Referring to FIG. 3 with continued reference to FIG. 1, if the preliminary beamforming occurs in the US probe 12 and the probe 12 includes standard connector technology (e.g., USB or the like), a possible embodiment may include an adaptor device 240. Individual channels 220 or lines 1-$n$ from/to the probe 12 are input to the adaptor 240 through a signal conversion block 206, and input to/from the console 50 through signal conversion block 208. The signal conversion blocks 206, 208 convert the signals to/from the probe 12 or to/from the console 50 as needed so that the adaptor device 240 will be compatible with USB interfaces or whatever interface/connector technology is employed. For example, in tablet US systems, the US probe 12 is connected to the tablet PC via a USB interface. In this case, the adaptor device 240 also has USB interfaces 206 and 208. In the adaptor device 240, individual beam signals are extracted from the USB standard and used to construct the trigger signals 112, 114 as described above.

The signals from the individual channels 220 of an image are employed to construct the frame trigger signal 114 and line trigger signals 116. For example, the signal corresponding to a first line (line 1) can be used to generate the frame trigger signal 114. Similarly, the signal from every line (lines 1-$n$) is used to generate line trigger signals 116. The frame and line trigger signals 114, 116 are output from the adaptor device 240 through ports which are accessible externally. The individual US beams are also output and connect directly to the US console 50 through signal conversion block 208. Thus, the US imaging functionality remains unaltered.

The adaptor device 240 may include a semiconductor chip or printed circuit board (PCB) 202 onto which a plurality of metallizations 204 are formed using processing techniques known in the art. In the embodiment depicted in FIG. 3, pulse generator circuits 110 and 112 may be formed, using semiconductor processing, concurrently during the formation of the metallizations 204. Alternately, the pulse generators 110, 112 may be added by chip bonding or other process.

Channels 220 are interconnected to lines 230, which connect to the pulse generators 110, 112. Upon receiving the signals on channels 220, lines 230 provide input to the respective pulse generator 110, 112. The interconnections between channels 220 and lines 230 may include direct connections, switches, multiplexers, etc.

Figure 4:
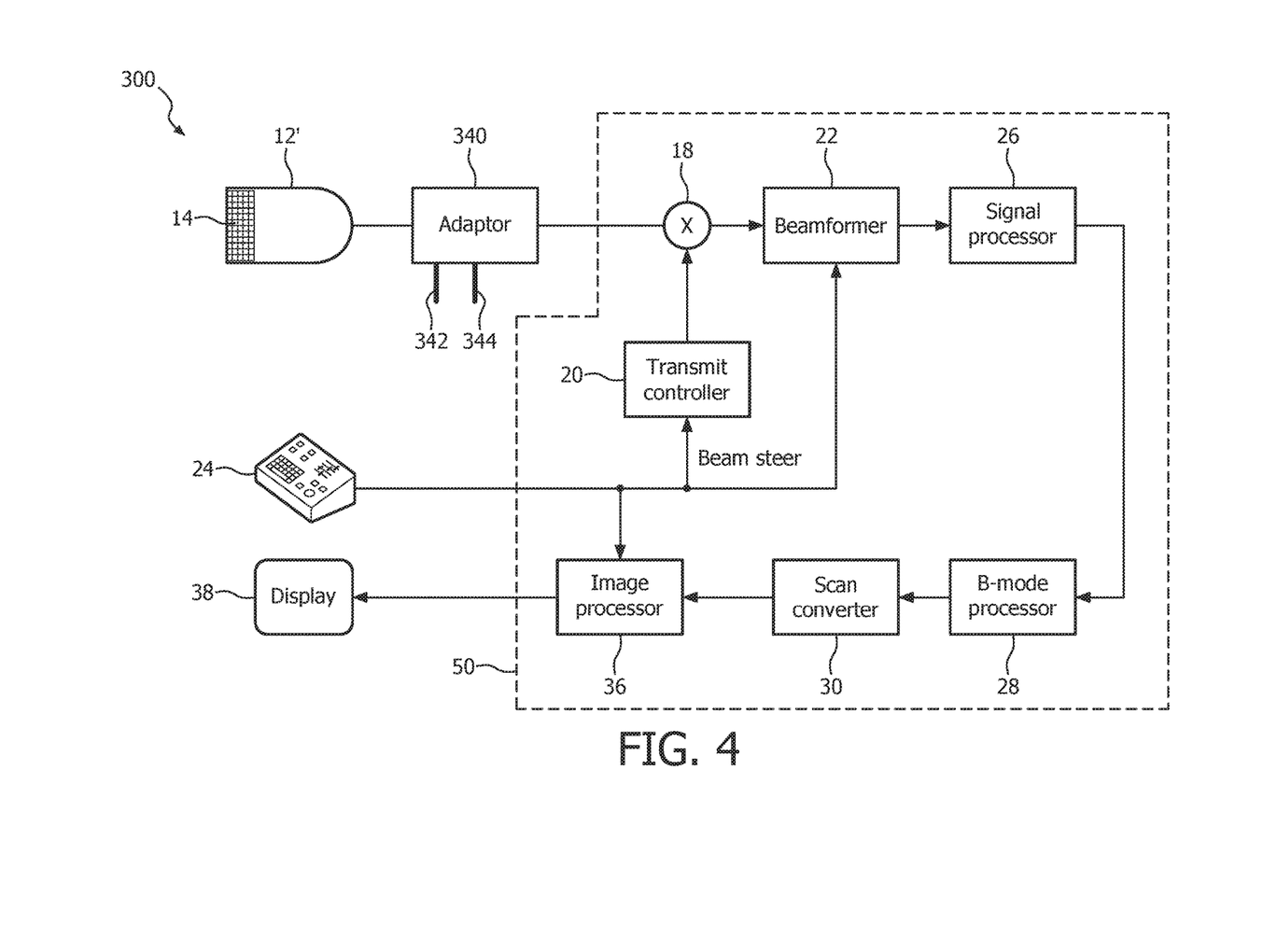
FIG. 4 is a block diagram showing an ultrasound system without preliminary beamforming in a probe and including an adaptor device in accordance with another embodiment.

Referring to FIG. 4, an ultrasound imaging system 300 constructed in accordance with the present principles is shown in block diagram form. The ultrasound system 300 includes a transducer device or probe 12' having a transducer array 14 for transmitting ultrasonic waves and receiving echo information. In this embodiment, the probe 12' does not perform any preliminary beamforming. If the preliminary beamforming does not occur in the US probe 12, the received voltage signals output from each piezoelectric element in array 14 can be utilized to generate the frame and line trigger signals on lines 342 and 344 in an adaptor device 340. In US systems, each line in a US image is constructed by appropriately delaying an input pulse signal to individual transducer elements in the probe 12'. By knowing, a priori, these delays for individual lines, a current line number can be identified by analyzing the time delays associated with the received voltages from each transducer element in array 14.

In one embodiment, delays can be reported to the adaptor device 340 by the transmit controller 20. Logic circuits to determine the triggers from the signal delays can reside inside the adaptor device 340. In one embodiment, instead of being between the probe 12' and the console 50, the adaptor device 340 may be at stand-alone location that communicates with the transmit controller 20 directly to output the trigger signals.

When a first line in the image is identified having a delay corresponding with the reported delay of the transmit controller 20, a frame trigger signal and a line trigger signal are generated on lines 342 and 344 using a pulse generator circuit. When each subsequent line is identified, a line trigger signal 344 is generated.

Figure 5:
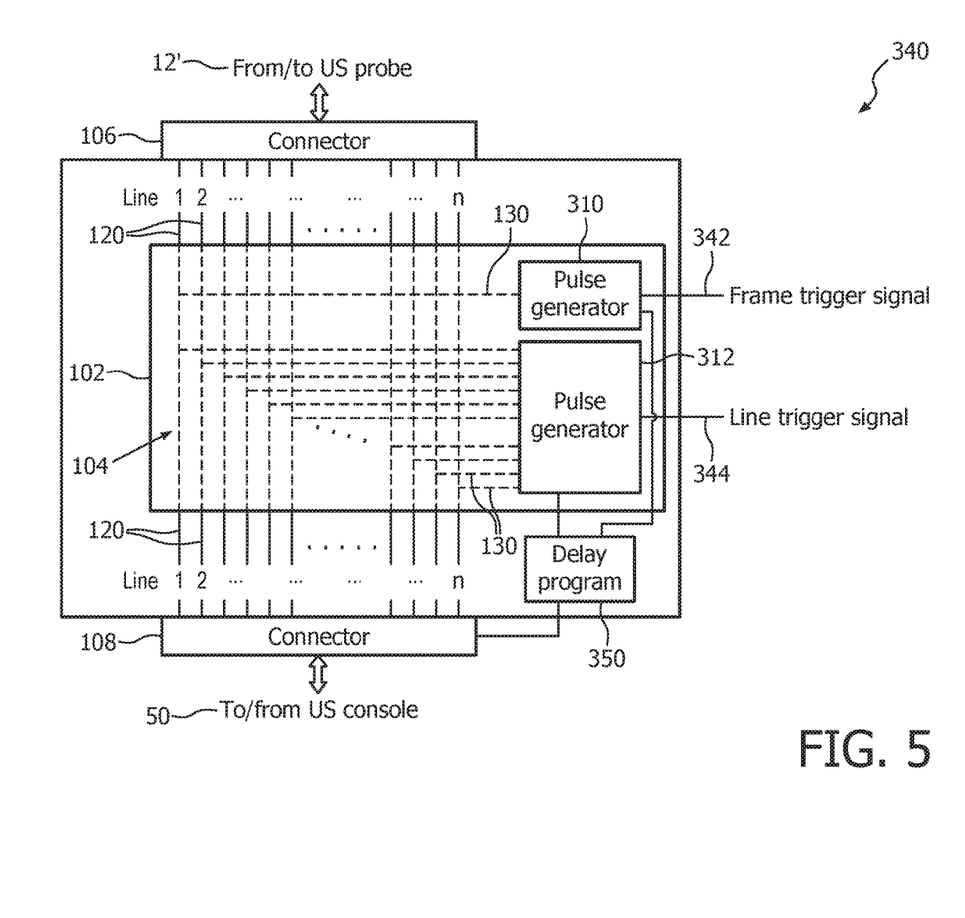
FIG. 5 is a schematic block diagram showing an adaptor device with a delay program for matching delays with input signals to determine trigger signal timing in accordance with another embodiment.

Referring to FIG. 5, the adaptor device 340 is shown in greater detail in accordance with one illustrative embodiment. When the preliminary beamforming does not occur in the US probe 12', received voltage signals output from each piezoelectric element of array can be utilized to generate the frame and line trigger signals, if the voltage signals are compared with input information about delay, to make a comparison to determine trigger signals.

Each line in the US image is constructed by delaying an input pulse signal to individual transducer elements. The input pulse signal is sent through the adaptor device 340 (e.g., from transmit controller 20, FIG. 1). The delays for individual lines are known in advance and may be programmed into a program delay module or circuit 350. The current line number (lines 1-$n$) can be identified by analyzing the time delays associated with the received voltages from each transducer element. In other words, when a delay is expected (as is known from the delay program 350), the received voltage is compared with the delay to identify when the frame is updated (to generate a frame trigger signal) and when subsequent lines are updated. When the first line in the image is identified, a frame trigger signal and a line trigger signal are generated using pulse generator circuits 310 and 312. When each subsequent line is identified, a line trigger signal is generated.

Depending on which scan line is being generated and the depth along that scan line, there are specific time delays associated with each element on the US probe 12'. Therefore, decision making by delay program 350 can be as simple as comparing the current time delays on the elements to a pre-populated database, to make a determination of when a line/frame is first fired. The output of this can be a binary input to the pulse generators 310, 312 for the line and frame trigger signals (e.g., 1=generate triggers, 0=no trigger).

Figure 6:
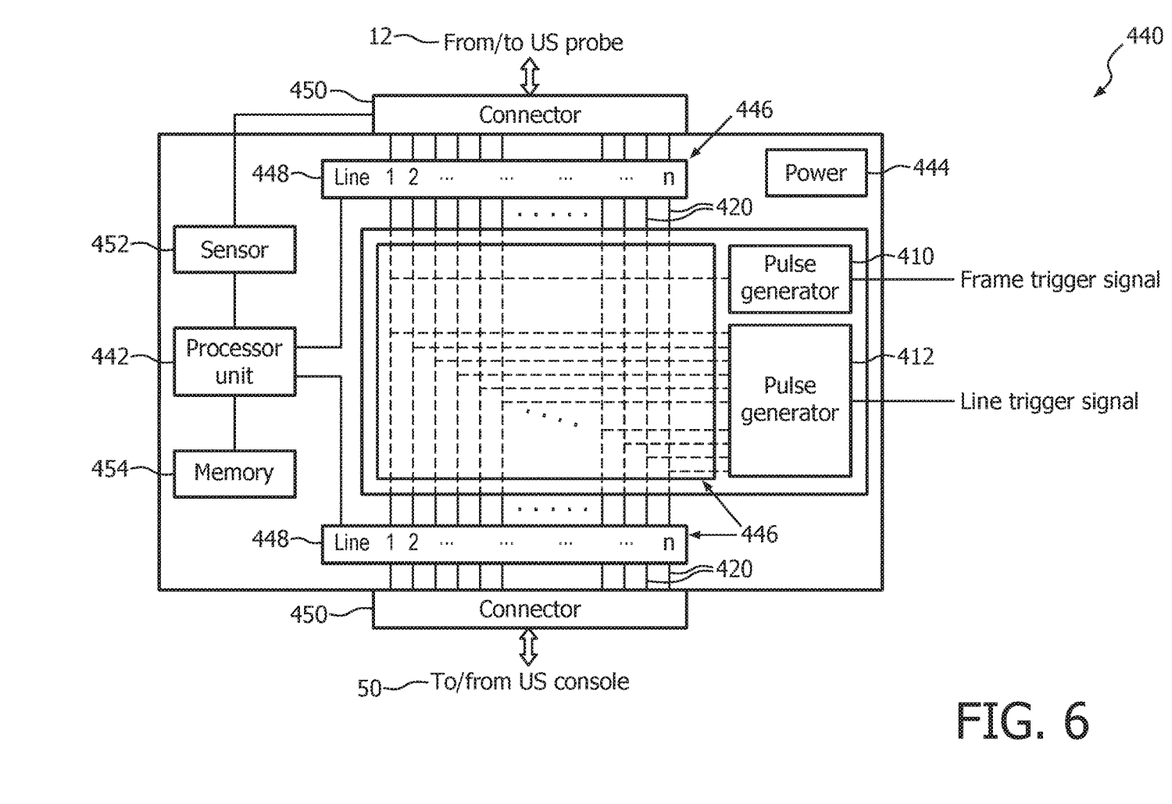
FIG. 6 is a schematic block diagram showing an adaptor device with a processor, power source and logic circuits in accordance with another embodiment.

Referring to FIG. 6, another adaptor device 440 provides additional features and functions in accordance with the present principles. The adaptor device 440 may include a processing unit or controller 442 (e.g., a field programmable gate array (FPGA) or micro-processor) configured to process input signals to create the frame/line triggers signals. The processing unit 442 may include an integrated circuit chip, a combination of analog circuits or a combination of the two. A memory array or device 454 may be included to assist in computations, encoding/decoding and to store applications or provide other functions for the adaptor device 440.

The adaptor device 440 may include a power source 444 in the form of a wired connector from an external power source or a built-in battery into the adapter device 440. Power from the power source 444 may be employed to run logic or the processing unit or for other computations. In some cases, a power line exists between the US console (scanner) and probe, the power could be derived from this power line. The power could be employed to run any aspect of the adaptor device 440, for example, run multiplexing circuits 446 associated with channel lines 420 and pulse generator circuits 410 and 412. The multiplexing circuits 446 may include logic circuits 448 employed to ensure that there is no loss in signal from the console (scanner) to the probe, from the addition of the adaptor device 440.

In another embodiment, the power source 444 could be used to transmit the trigger signals over a wired or wireless communication link 450.

In some embodiments, a micro-beamformer might be implemented in the probe to compress the number of lines in the connection between the scanner (console) and the probe. In such cases, instead of reading individual signals to generate the trigger signals, a more complex logic circuit 448 could combine the different line signals to generate the trigger signals. This complex logic circuit 448 could be proportional to the direct electrical properties of the signals, or could combine these properties into more computationally involved computations.

In some embodiments, the power drawn by the probe 12 (e.g., for firing the acoustic signals) could be an indication of the formation of a new trigger signal (frame or line). Most US probes do not have a power-source or significant power storage capability inside the probe. Note that power is needed to fire the acoustic pulses with a minimum signal strength.

In other embodiments, the logic circuits 448 may include encoding and decoding capabilities. Some of the individual signals could be encoded, and a decoding algorithm could extract out the time points for creating the requisite frame/line triggers. In some embodiments, a chip on the US probe (12) may be provided to generate the trigger signals. This chip in some cases could be an FPGA type processor. In these cases, the FPGA could be reprogrammed to route the trigger signals in a special way so as to communicate them to the adaptor device 440.

In still other embodiments, natural leakage currents from the original signal could be detected and used to estimate the trigger signals, e.g., using a sensor circuit 452. The sensor circuit 452 could be integrated inside the adaptor device 440 or might remain partially outside (like antennae on the probe cable). All or some parts of the processing unit 442 can be designed to stay partially outside the adaptor device 440. However, in other cases processing unit 442 may stay completely inside for ease of use.

In one embodiment, sensor circuit 452 may be employed as an external antenna on the US cable (12) that can detect 'leakage' currents or passing of high voltages. Alternately, some special circuitry (e.g., in logic circuits 448) in the adapter device 440 could be sensitive to high variations in current/voltage. When these high variations are detected, another circuit (e.g., pulse generators 410, 412) in the adapter device 440 could generate frame/line triggers (this will correlate to passing of high voltage/current/energy every time a new beam is fired by the US scanner). The variations themselves could be detected in a single (or using multiple) wires. This may include detecting higher voltages, currents, energy or other similar variants.

The adaptor device 440 may be physically integrated within the probe 12 (FIG. 1), with the console 50 (FIG. 1), a cable or interface between them, or may be designed to fit into an external fixture like a table. In such a case, the US probe adapter 440 could also be integrated into this fixture, which could then have a separate link 450 (wired or wireless) to the console. This fixture could have additional links for signal communication to other tracking systems/software.

Some compact US systems utilize wireless transmission between the US probe and console. In such a case, most of the beamforming occurs in the US probe. Therefore, the adaptor device 440 may be made compatible with wireless US systems. In one embodiment, the adaptor device 440 may be attached to the US probe 12 (FIG. 1). The adaptor device 440 has the ability to interpret/decode the image data formed in the US probe 12 and generate the frame and line trigger signals. The frame and line trigger signals can be transmitted wirelessly through link 450, although the trigger signal transmission can still be wired. In another embodiment, the adaptor device 440 may be attached to the US console 50 and include the ability to wirelessly receive image data from the probe 12 and generate the frame and line trigger signals. The frame and line trigger signals can be transmitted using a wireless or wired protocol.

It should be understood that the features of one disclosed embodiment may be included in other disclosed embodiments and that any combination of features may be provided in accordance with the present principles. The present principles may use the trigger signals for applications such as, e.g., tracking a tool in ultrasound image space, to synchronize equipment with US images, etc.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for apparatuses for obtaining trigger signals from ultrasound systems (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:
1. An adaptor device, comprising:
a first connector configured to establish at least electrical communication with an ultrasound probe;
a second connector configured to establish at least electrical communication with an ultrasound console;
an array of lines connecting the first connector to the second connector, the array of lines passing one or more signals of the ultrasound probe from the first connector to the second connector;
at least one pulse generator configured to receive the one or more signals from at least one line of the array of lines and to generate at least one trigger signal responsive to the received one or more signals; and an external output port connected to the at least one pulse generator, wherein the at least one trigger signal is output from the adaptor device through the external output port.

2. The device as recited in claim 1, wherein at least one of the first connector and the second connector includes a signal converter to permit interface compatibility between different signal protocols.

3. The device as recited in claim 1, wherein at least one of the first connector and the second connector includes a wireless link.

4. The device as recited in claim 1, wherein the at least one pulse generator includes a pulse generator to generate a frame trigger signal and a pulse generator to generate a line trigger signal.

5. The device as recited in claim 1, wherein the external output port includes a wireless link.

6. The device as recited in claim 1, wherein the array of lines connecting the first connector to the second connector provide a direct physical and electrical connection between the ultrasound probe and the ultrasound console.

7. The device as recited in claim 1, further comprising a delay program configured to compare transducer signal delays from the ultrasound probe with expected delays to enable the at least one pulse generator to output the at least one trigger signal.

8. The device as recited in claim 1, further comprising a power source configured to power on-board features of the adapter device.

9. The device as recited in claim 1, further comprising a processing unit configured to process input signals from the ultrasound probe.

10. The device as recited in claim 9, wherein the processing unit is programmed to at least one of: encode the one or more signals, decode the one or more signals, multiplex or reroute the one or more signals or perform computations on the one or more signals.

11. An adaptor device, comprising:
a first connector for interfacing with an ultrasound probe;
a second connector for interfacing with an ultrasound console;
an array of lines connecting the first connector to the second connector;
at least one pulse generator configured to generate at least one trigger signal responsive to a signal on one or more of the array of lines;
an external output port for outputting the at least one trigger signal; and
a line sensor configured to detect current on a line or cable coupled to the adapter device and estimate the at least one trigger signal based on the current detected.

12. An adaptor device, comprising:
a first connector configured to establish at least electrical communication with an ultrasound probe;
a second connector configured to establish at least electrical communication with an ultrasound console;
an array of lines formed on a substrate and connecting the first connector to the second connector, the array of lines passing a plurality of signals from the ultrasound probe from the first connector to the second connector;
a frame pulse generator configured to receive a signal of the plurality of signals from a line of the array of lines designated to indicate a new frame, and to generate a frame trigger signal responsive to the signal;
a line pulse generator configured to receive the plurality of signals from the array of lines, and to generate line trigger signals responsive to plurality of signals; and
external output ports connected to the frame pulse generator and the line pulse generator, wherein the frame and line trigger signals are output from the adaptor device through the external output ports, respectively.

13. The device as recited in claim 12, wherein at least one of the first connector and the second connector includes a signal converter to permit interface compatibility between different signal protocols.

14. The device as recited in claim 12, wherein at least one of the first connector and the second connector includes a wireless link.

15. The device as recited in claim 12, wherein the external output includes a wireless link.

16. The device as recited in claim 1, wherein at least one of the first connector and the second connector is selectively removable from the ultrasound probe and the ultrasound console, respectively.

17. The device as recited in claim 12, wherein at least one of the first connector and the second connector is selectively removable from the ultrasound probe and the ultrasound console, respectively.

* * * * *